US00PP09024P

United States Patent [19]

Mantel

[11] Patent Number: Plant 9,024

[45] Date of Patent: Dec. 27, 1994

[54] LILIUM BLAZING DWARF

[76] Inventor: Homme Mantel, P.O. Box 1314, Sandy, Oreg. 97055

[21] Appl. No.: 238,029

[22] Filed: May 4, 1994

[51] Int. Cl.[5] ..... A01H 5/00

[52] U.S. Cl. ..... Plt./87.4

[58] Field of Search ..... Plt. 87.4

*Primary Examiner*—James R. Feyrer

[57] ABSTRACT

A new variety of hybrid lily plant bearing large up-facing flowers of excellent form, long persistence, and exceptional substance. The new hybrid is particularly characterized by a compact racemose inflorescence of upfacing flowers of vibrant unspotted orange-red color, borne on a short, sturdy stem. This combination is completely new in the Asiatic hybrid divisions of lilies suited to forcing and to mass commercial cultivation. The variety is highly resistant to fusarium disease and shows tolerance of virus. The bulbs may be precooled and forced into flower under glass out of season. The clone is vigorous and is a good grower and propagator.

1 Drawing Sheet

BACKGROUND OF THE INVENTION

My new variety of lily plant originated as a seedling, which first flowered in Hood River, Ore. in 1989. The breeding efforts had as their objective the production of Asiatic hybrid lilies with upfacing orange and red flowers borne on short stems and suited to forcing into flower out of season for use as pot plants, heretofore unknown in the lily breeding art.

I achieved the desired objective by pollinating Lilium 'Orange Pixie' (U.S. Plant Pat. No. 5,792) with pollen of an unnamed outfacing red-orange seedling. I selected this clone at the time of its first flowering at the Boring, Ore. field of Columbia-Platte Lilies, Inc.; I purchased the only bulb of this clone and immediately removed it from the field. This seedling was a genetically unique third-generation *Lilium pumilum* hybrid with an exceptionally high bud count, brilliant red-orange flowers, and an early flowering time. The flowers of my new lily are characterized by an upfacing orientation, large size and exceptional substance, and a brilliant orange-red color. The new clone possesses unusually short, stout, strong stems and bears a compact racemose inflorescence with an unusually high bud count. In addition, it possesses to a high degree desirable characteristics of hybrid vigor. The clone is a good grower and propagator, as observed at Hood River and at Sandy, Ore.

My new variety of lily plant has been asexually reproduced by me and under my direction at Hood River and at Sandy, Ore. Successive generations produced by natural propagation from bulblets, by bulb scale propagation, and by tissue culturing from bulb scale explants have demonstrated that the novel and distinctive characteristics of my new variety are fixed and hold true under asexual propagation from generation to generation.

DESCRIPTION OF THE DRAWING

My new variety of lily plant is illustrated in the accompanying photographic (top) drawing, which shows the open bloom in full color and illustrates the flower form, the tepal arrangement, and (bottom) in particular the novel and distinctive short, sturdy stem bearing a compact racemose inflorescence with an unusually high bud count.

DESCRIPTION OF THE NEW VARIETY

The following is a detailed description of my new variety of Asiatic hybrid lily, with nomenclature according to the *International Lily Register* (Royal Horticultural Society of London, Second Edition, 1969), and with color designations according to the Colour Chart of The Royal Horticultural Society, published by the Society in 1966.

THE PLANT

Origin: Seedling.

Seed parent: Lilium 'Orange Pixie' (U.S. Plant Pat. No. 5,792).

Pollen parent: Unnamed Asiatic Seedling with many outfacing brilliant orange-red flowers.

Commercial classification: Hybrid Lilium clone.

Horticultural classification: Division IA, Upright Asiatic hybrid lily, according to the Horticultural Classification of Lilies, Royal Horticultural Society of London.

Form: Single stem, erect and stately.

Height: 20 to 50 cm from bulbs 14 to 18 cm in circumference, provided their light levels are adequate; low light levels may cause "stretching."

Growth: Vigorous and upright.

Foliage quantity: Abundant.

Size of leaf: 8 to 12 cm long×1.5–2.5 cm wide.

Shape of leaf: Lanceolate (pointed).

Texture: Leathery and glossy; exceptionally thick.

Color: Medium to dark green, lighter on lower side.

Bulb size: Any size, ranging to 25 cm circumference commercially.

Bulb color: White, with flushes of pink or yellow after exposure to light.

THE BUD

Form: Obtuse, ovoid, and long.

Size: 7 to 9 cm long and 8 to 11 cm in circumference just prior to opening.

Opening: Bud opens slowly, in response to morning light; this takes about one hour.

Color: RHS CC orange-red 30C to 33C, slightly lighter at base and apex.

Peduncle: Averages 1 to 3 cm, but it may elongate if light levels are too low or if bulbs have been improperly stored prior to facing. Color is deep green with a purple overlay.

THE FLOWER

Blooming habit: Annually in midseason; flowers once and profusely.

Size: Flowers are large-sized, averaging 15 to 17 cm in diameter, reflexing at the tips on the second day to 14 to 16 cm in diameter. The tepals are broad: outer tepals are 1.75 to 2.5 cm wide at the center, and the inner tepals are 2.25 to 3 cm wide at the center.

Borne: In a single compact racemic inflorescence producing 6 to 10 flowers from a bulb 14 to 16 cm in circumference.

Shape: Flowers form an open bowl with only slightly recurved tepal tips. Tepals are unusually thick and slightly cup-shaped.

Tepalage: Typical of genus Lilium, with 6 imbricated tepals.

Tepal color: RHS CC orange-red 33 A-B, shading to 30 A-B when light levels are lower and temperatures higher. The exceptional tepal thickness gives an exceptionally intense color.

Tepal spotting: Tepals have small, inconspicuous spots at their bases.

Tepal longevity: Tepals stay on stems about three weeks.

Pedicel length: Average 3 to 6 cm long.

Pedicel color: Dark green with purple overlay, appearing almost black when moderate temperatures and high light intensities favor anthocyanin formation.

Pedicel form: Exceptionally sturdy and somewhat ascending.

Color changes: Flowers become slightly less orange-red and more orange as the flowers age.

Appearance: Flower is shiny.

Disease resistance: The flower and plant are resistant to disease; in particular, they are resistant to Fusarium bulb rot and Botrytis blight.

Fragrance: None.

Lasting quality: The flower is long lasting.

THE REPRODUCTIVE ORGAN

Stamens: Arrangement typical of genus Lilium. Six stamens with soft orange-red (RHS CC orange-red 30 D) filaments 8 to 10 cm long.

Pollen and anthers (dehisced): RHS CC greyed orange 171 A-172 A.

Pistil: One in number, 6 to 8 cm long, RHS CC orange 30 D.

Stigma: Small in size, RHS CC greyed red 180 C-D.

Characteristics of ovary: Characteristic of genus Lilium.

THE FRUIT

Fertility: The fruit bears fertile seed when pollinated with tetraploid Asiatics.

Shape: Ovoid.

Color at maturity: Soft brown, sometimes overlaid with soft plum.

My new variety of Asiatic hybrid lily most nearly resembles 'Orange Pixie,' but it has larger, broader-petalled flowers of much greater substance, a deeper and more red-orange color, and a much higher bud count. It is generally fertile when crossed with tetraploid Asiatics, unlike 'Orange Pixie.'

I claim:

1. A new and distinctive variety of Asiatic hybrid lily plant substantially as herein shown and described, characterized by its high resistance to disease; its tolerance of virus; its vigorous growth and rapid natural propagation; the excellence of its flower form, size, and substance; its versatility both as a garden plant and as a pot plant produced from pre-cooled bulbs forced under glass out of season; and in particular by its unique short, sturdy stem with compact racemose inflorescence bearing an exceptionally large number of brilliant orange-red upfacing flowers of unusual thickness and color intensity, a combination unique among Asiatic hybrid lilies suited to forcing and to mass commercial cultivation.

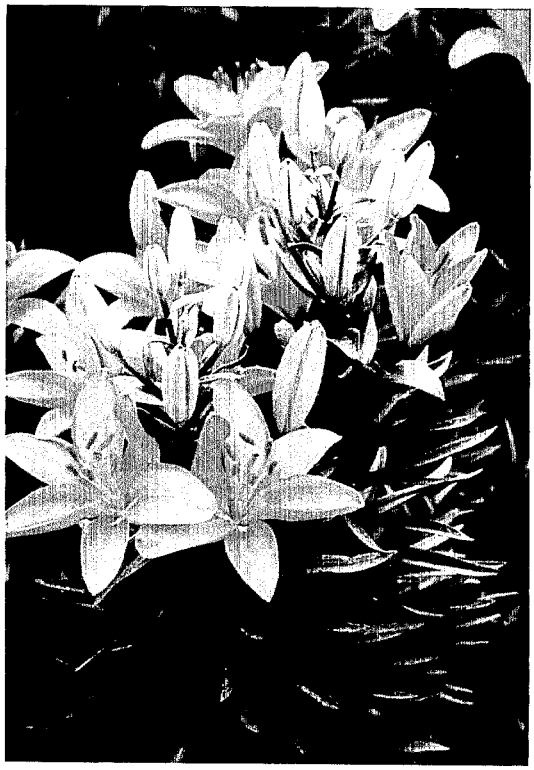
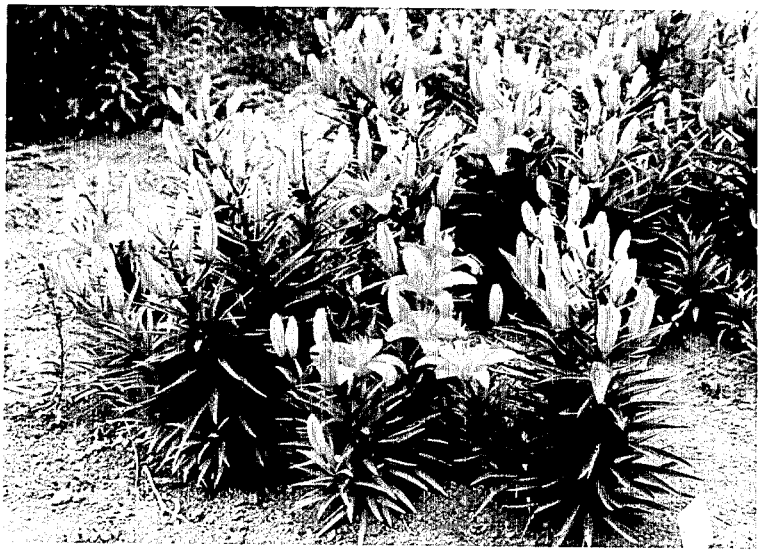

* * * * *